United States Patent
Oliver

(10) Patent No.: US 7,850,724 B2
(45) Date of Patent: *Dec. 14, 2010

(54) SELF-EXPANDING STENT DELIVERY SYSTEM

(75) Inventor: Ruetsch Oliver, Neuhausen (CH)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 1015 days.

This patent is subject to a terminal disclaimer.

(21) Appl. No.: 11/646,211

(22) Filed: Dec. 26, 2006

(65) Prior Publication Data

US 2007/0106367 A1     May 10, 2007

Related U.S. Application Data

(63) Continuation of application No. 10/655,615, filed on Sep. 5, 2003, now Pat. No. 7,175,650.

(30) Foreign Application Priority Data

Sep. 9, 2002 (EP) ................... 02020170

(51) Int. Cl.
A61F 2/06 (2006.01)

(52) U.S. Cl. .................................. 623/1.12

(58) Field of Classification Search ........... 623/1.11, 623/1.12, 1.2; 606/191–198, 200
See application file for complete search history.

(56) References Cited

U.S. PATENT DOCUMENTS

| | | | |
|---|---|---|---|
| 5,571,135 A * | 11/1996 | Fraser et al. ........... | 623/1.12 |
| 5,976,153 A | 11/1999 | Fischell et al. | |
| 6,254,609 B1 | 7/2001 | Vrba et al. | |
| 6,331,186 B1 | 12/2001 | Wang et al. | |
| 6,443,979 B1 | 9/2002 | Stalker et al. | |
| 6,517,547 B1 * | 2/2003 | Feeser et al. ........... | 606/198 |

(Continued)

FOREIGN PATENT DOCUMENTS

EP        0 839 504 A1     6/1998

(Continued)

OTHER PUBLICATIONS

U.S. Appl. No. 10/655,615, mail date May 3, 2006, Office Action.

(Continued)

*Primary Examiner*—Kevin T Truong
(74) *Attorney, Agent, or Firm*—Workman Nydegger

(57) ABSTRACT

A stent delivery system delivers a self-expanding stent to a predetermined location in a body lumen. The delivery system has a catheter body, a retractable outer sheath and a proximal retraction handle connected to a proximal end of the catheter body. The catheter body carries the stent near a distal end of the catheter body for transporting the stent for deployment. The sheath surrounds and contains the stent in a delivery configuration where the stent has a reduced radius along its entire axial length. The sheath has an outer tube a separate inner tube. The outer tube has a distal end portion surrounding the stent along its entire length and a proximal end portion connected to the retraction handle. The inner tube is disposed concentrically within the outer tube and has a distal end portion surrounding the stent only along a part of its entire length.

24 Claims, 2 Drawing Sheets

U.S. PATENT DOCUMENTS

| | | |
|---|---|---|
| 6,602,280 B2 | 8/2003 | Chobotov |
| 2001/0047150 A1 | 11/2001 | Chobotov |

FOREIGN PATENT DOCUMENTS

| | | |
|---|---|---|
| WO | WO 98/23241 | 6/1998 |
| WO | WO 02/22024 A2 | 3/2002 |

OTHER PUBLICATIONS

U.S. Appl. No. 10/655,615, mail date Oct. 4, 2006, Notice of Allowance.

U.S. Appl. No. 10/655,615, mail date Jan. 24, 2007, Issue Notification.

* cited by examiner

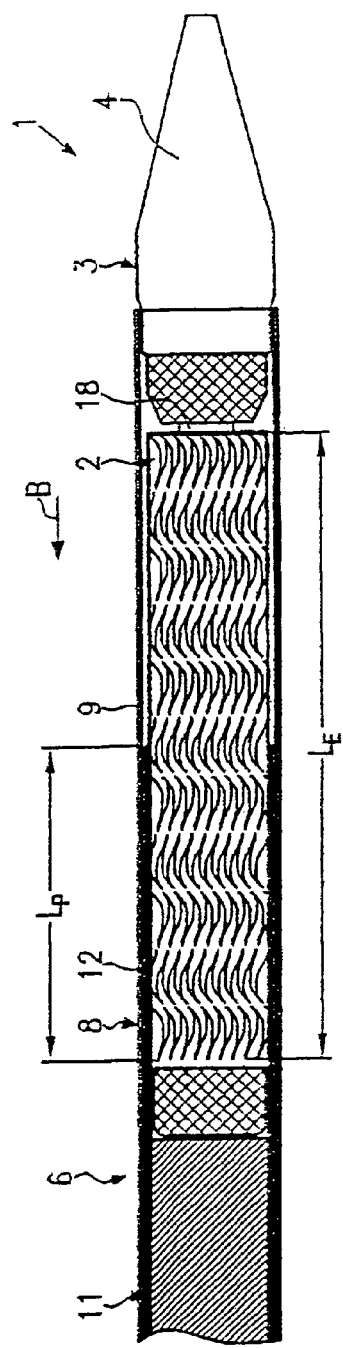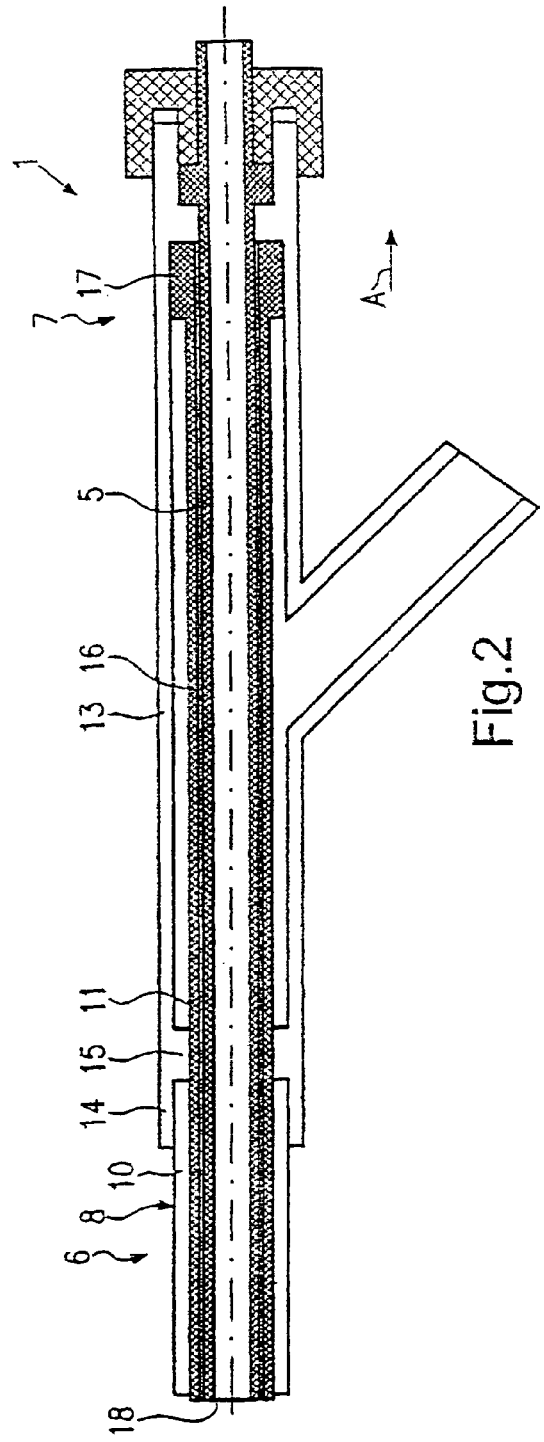

SELF-EXPANDING STENT DELIVERY SYSTEM

BACKGROUND OF THE INVENTION

1. Field of the Invention

The present invention generally relates to a self-expanding stent delivery system for delivering a self-expanding stent.

2. Background Information

Delivery systems for deploying endovascular stent grafts, self-expanding stents or balloon expandable stents are well-known in the field of medical technology. One example of a stent delivery system for delivering a self-expanding stent is disclosed in International Patent Publication No. WO 98/23241, which corresponds to U.S. Pat. No. 5,968,052.

As has been explained in the before-mentioned citation a self-expanding stent is a stent which expands from a compressed delivery position to its original diameter when released from the delivery device, exerting radial force on the constricted portion of the body lumen to re-establish patency. One common self-expanding stent is manufactured of nitinol, a nickel-titanium shape memory alloy, which can be formed and annealed, deformed at a low temperature, and recalled to its original shape with heating, such as when deployed at body temperature in the body.

One important factor in delivering the stent is a controlled precise retraction of the retractable outer sheath. What is needed is a delivery system which provides for a controlled and precise retraction of the retractable outer sheath and enabled the physician to accurately determine proper positioning of the stent, as well as track the retraction of the outer sheath.

Known delivery systems suffer, however, from the draw-back that the retraction forces are often too high, especially in cases where the stents are covered with layers made from body-compatible materials or the like so that the friction forces between the stent and the outer sheath may become excessively high.

In view of the above, it will be apparent to those skilled in the art from this disclosure that there exists a need for an improved self-expanding stent delivery system for delivering a self-expanding stent. This invention addresses this need in the art as well as other needs, which will become apparent to those skilled in the art from this disclosure.

SUMMARY OF THE INVENTION

Therefore one object underlying the present invention is to provide a self-expanding stent delivery system for delivering a self-expanding stent that is able to overcome the before-mentioned draw-back so that a smooth retraction of the retractable outer sheath is possible.

Basically, the above object is attained by providing a self-expanding stent delivery system according to the present invention that comprises a retractable outer sheath that is divided into an outer tube and a separate inner tube. The tubes are disposed concentrically with respect to each other. The outer tube surrounds and covers the stent along its entire length whilst the separate inner tube surrounds the stent only partly, as especially only along about 50% of its entire length.

This simple and effective arrangement results in the advantage that the surface between the stent and the outer sheath is reduced by a remarkable percentage, especially up to 50%, so that the retraction forces become significantly smaller.

A specifically advantageous embodiment provides for an arrangement of stop members. One of the stop members can be disposed at the distal end of a retraction tube of the retraction handle whilst the second stop member is disposed at the proximal end portion of the inner tube. So, upon operation of the retraction handle the outer tube is retracted and after a predetermined length of retraction the stop members engage each other so that also the inner tube can be retracted upon only one operation of the retraction handle so that the physician can deploy the stent with the same kind of operation as with conventional delivery systems but much smoother and with lower retraction forces. This facilitates an exact position of the stent as the stent is prevented from being longitudinally compressed.

According to the present invention, the outer tube may be a co-extruded tubing, e.g., made from polyamid whilst the inner tubing is preferably made from polyethylene.

In general, the materials of the tubes are to be chosen from combinations of materials that result in low friction resistance. Alternatively, the materials of the tubes are tubings comprising layers with low friction coefficients.

These and other objects, features, aspects and advantages of the present invention will become apparent to those skilled in the art from the following detailed description, which, taken in conjunction with the annexed drawings, discloses a preferred embodiment of the present invention.

BRIEF DESCRIPTION OF THE DRAWINGS

Referring now to the attached drawings which form a part of this original disclosure:

FIG. 1 is a schematically simplified side cross sectional view of a distal end portion of a self-expanding stent delivery system according to a first embodiment of the present invention;

FIG. 2 is a schematically simplified side cross sectional view of a proximal end portion of the self-expanding stent delivery system illustrated in FIG. 1 according to the present invention.

DETAILED DESCRIPTION OF THE PREFERRED EMBODIMENTS

Figure 3:
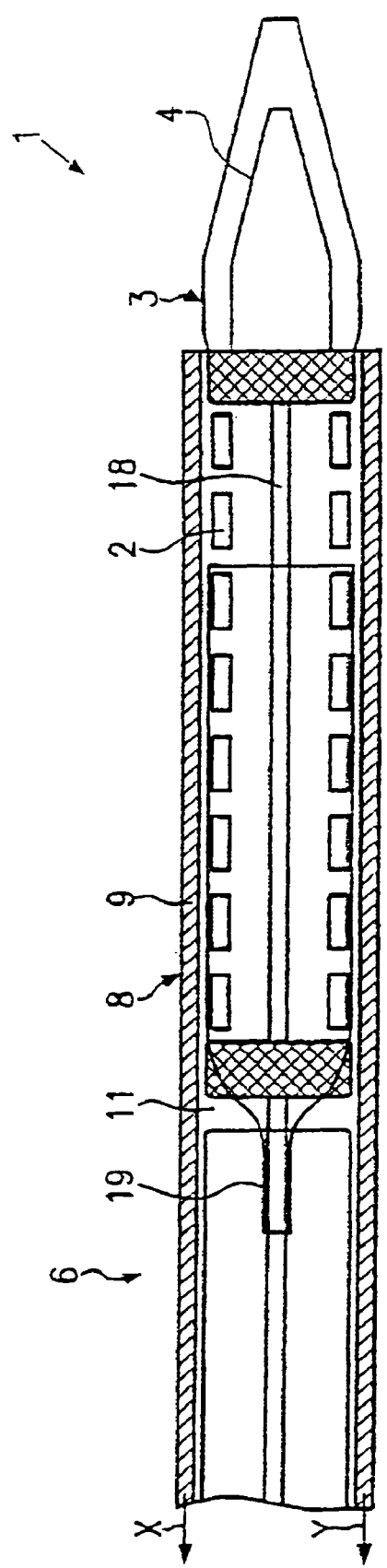
FIG. 3 is a schematically simplified side cross sectional view, similar to FIG. 1, of a distal end portion of a self-expanding stent delivery system of a second embodiment of the present invention.

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Referring initially to FIGS. 1 and 2, a self-expanding stent delivery system 1 is illustrated in accordance with a first embodiment of the present invention. The delivery system 1 is intended for delivering a self-expanding stent 2 shown in elevation in FIG. 1.

The delivery system 1 basically comprises a catheter body 3 having a proximal end 5 and a distal end 4. The catheter body 3 is adapted to transport the stent 2 to a predetermined site in a body lumen for deployment that is not shown in FIGS. 1 and 2.

The catheter body 3, furthermore, comprises a metal and/or a metal-polymeric and/or a polymeric shaft 18 that extends from the proximal end 5 to the distal end 4.

The delivery system 1, furthermore, comprises a retractable outer sheath 6 shown in FIGS. 1 and 2 that surrounds the stent 2 and contains the stent 2 in a delivery configuration where the stent 2 has a reduced radius along its entire length $L_E$ shown in FIG. 1.

FIG. 2 shows a proximal retraction handle 7 that may be configured as an integral part of a so-called Tuohy Borst valve. The handle 7 is disposed at the proximal end 5 of the catheter body 3 as shown in FIG. 2.

According to the present invention the sheath 6 is a combination of an outer tube 8 and a separate inner tube 11. The outer tube 8 has a distal end portion 9 that surrounds the stent 2 along its entire length $L_E$ as can be learned from FIG. 1.

The outer tube 8, furthermore, comprises a proximal end portion 10 being connected to the retraction handle 7, e.g. by an adhesive connection.

The separate inner tube 11 is disposed concentrically within the outer tube 8 and concentrically surrounds the metal shaft 18 of the catheter body 3. The inner tube 11 comprises a distal end portion 12 surrounding the stent 2 only along a part $L_P$ of its entire length $L_E$ as can be seen form FIG. 1. This configuration significantly reduces the friction forces between the stent 2 and the outer sheath 6 so that the forces for retraction of the outer sheath 6 become remarkably smaller in comparison to conventional delivery systems.

The handle 7 of the preferred embodiment shown in FIGS. 1 and 2 comprises a retraction tube 13 that is connected at its distal end 14 to the proximal end portion 10 of the outer tube 8. The retraction tube 13 comprises a stop member 15 at its distal end 14 (see FIG. 2). The stop member 15 can be configured as an annular ring extending inwardly from the inner periphery of the retraction tube 13.

As can be seen from FIG. 2 the retraction tube 13 concentrically surrounds the proximal end portion 5 of the catheter body 3 and the proximal end portion 16 of the inner tube 11.

The inner tube 11, in turn, comprises a stop member 17 at its proximal end portion 16. The stop member 17 is alternately configured as an annular ring extending outwardly from the outer periphery of the inner tube 11.

As can be seen from FIG. 2 the stop members 15 and 17 are adapted to be engaged with one another upon retraction of the handle 17. When operating the retraction tube 13 of the handle 7 in the direction of arrow A in FIG. 2, the outer tube 8 is pulled back in the direction of arrow B shown in FIG. 1 to slide partly on the inner tube 11 as the inner tube 11 covers only a part of the stent 2. Upon engagement of the stop members 15 and 17, the inner tube 11 is also pulled back in the direction of arrow B shown in FIG. 1 so that stent 2 can be released and deployed at a predetermined site in a body lumen.

Second Embodiment

FIG. 3 depicts a second embodiment of a delivery system 1 according to the present invention. In view of the similarity between the first and second embodiments, the parts of the second embodiment that are identical or similar to the parts of the first embodiment will be given the same reference numerals as the parts of the first embodiment. Moreover, the descriptions of the parts of the second embodiment that are identical or similar to the parts of the first embodiment of FIGS. 1 and 2 may be omitted for the sake of brevity. Also, the proximal end portion illustrated in FIG. 2 is used with of the self-expanding stent delivery system of this second embodiment with slight modifications to accommodate the differences between the first and second embodiments.

The basic difference between the embodiments of FIG. 1 and FIG. 3 is to be seen in the fact that the inner tube 11 is fixed at a fixing portion 19 to the shaft 18 shortly after the stent 2 as seen in the direction of arrows X and Y. To retract inner tube 11, with this embodiment, it is possible to retract the shaft 18 after having retracted the outer tube 8.

The terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

This application claims priority to European Patent Application No. 02 020 10.3 filed on Sep. 9, 2002. The entire disclosure of European Patent Application No. 02 020 10.3 is hereby incorporated herein by reference.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents. Thus, the scope of the invention is not limited to the disclosed embodiments.

What is claimed is:

1. A self-expanding stent delivery system for delivering a self-expanding stent to a predetermined location in a body lumen, the self-expanding stent delivery system comprising:
   a catheter body having a proximal end and a distal end, the catheter body being configured and arranged to carry the stent near the distal end of the catheter body for transporting the stent to the predetermined location in the body lumen for deployment;
   a retractable outer sheath configured and arranged to surround the stent and contain the stent in a delivery configuration such that the stent has a reduced radius along its entire axial length; and
   a proximal retraction handle connected to the proximal end of the catheter body,
   the retractable outer sheath comprising the combination of:
      an outer tube having a distal end portion configured and arranged to surround the stent along the entire length of the stent and contain the stent in the delivery configuration, the outer tube having a proximal end portion being connected to the retraction handle, and
      a separate inner tube being disposed concentrically within the outer tube and having an end portion configured and arranged to surround the stent only along a part of the entire length of the stent.

2. The self-expanding stent delivery system according to claim 1, wherein the handle comprises a retraction tube being connected at its distal end to the proximal end portion of the outer tube.

3. The self-expanding stent delivery system according to claim 2, wherein the retraction tube comprises a stop member at its distal end.

4. The self-expanding stent delivery system according to claim 3, wherein the retraction tube concentrically surrounds the proximal end of the catheter body and a proximal end portion of the inner tube.

5. The self-expanding stent delivery system according to claim 2, wherein the retraction tube concentrically surrounds the proximal end of the catheter body and a proximal end portion of the inner tube.

6. The self-expanding stent delivery system according to claim 5, wherein the inner tube comprises a stop member at its proximal end portion that is adapted to be engaged with a stop member of the retraction tube upon retraction of the handle.

7. The self-expanding stent delivery system according to claim 6, wherein the inner tube surrounds the stent along about 40% to 60% of the entire length of the stent.

8. The self-expanding stent delivery system according to claim 7, wherein the separate inner tube is fixed to a shaft of catheter body.

9. The self-expanding stent delivery system according to claim 8, wherein the end portion of the inner tube is a distal end portion of the inner tube.

10. The self-expanding stent delivery system according to claim 1, wherein the inner tube surrounds the stent along about 40% to 60% of the entire length of the stent.

11. The self-expanding stent delivery system according to claim 1, wherein the stent is configured as a stent graft or a covered stent.

12. The self-expanding stent delivery system according to claim 1, wherein the separate inner tube is fixed to a shaft of catheter body.

13. The self-expanding stent delivery system according to claim 1, wherein the end portion of the inner tube is a distal end portion of the inner tube.

14. A self-expanding stent delivery system comprising:
a self-expanding stent;
a catheter body having a proximal end and a distal end, the catheter body being configured and arranged to carry the stent near the distal end of the catheter body for transporting the stent to a predetermined site in a body lumen for deployment;
a retractable outer sheath configured and arranged to surround the stent and contain the stent in a delivery configuration such that the stent has a reduced radius along its entire axial length; and
a proximal retraction handle connected to the proximal end of the catheter body, the retractable outer sheath comprising the combination of:
an outer tube having a distal end portion configured and arranged to surround the stent along the entire length of the stent and contain the stent in the delivery configuration, the outer tube having a proximal end portion being connected to the retraction handle, and
a separate inner tube being disposed concentrically within the outer tube and having an end portion configured and arranged to surround the stent only along a part of the entire length of the stent.

15. The self-expanding stent delivery system according to of claim 14, wherein the stent is configured as a stent graft or a covered stent.

16. The self-expanding stent delivery system according to claim 14, wherein the handle comprises a refraction tube being connected at its distal end to the proximal end portion of the outer tube.

17. The self-expanding stent delivery system according to claim 16, wherein the retraction tube comprises a stop member at its distal end.

18. The self-expanding stent delivery system according to claim 16, wherein the retraction tube concentrically surrounds the proximal end of the catheter body and a proximal end portion of the inner tube.

19. The self-expanding stent delivery system according to claim 18, wherein the inner tube comprises a stop member at its proximal end portion that is adapted to be engaged with the stop member of the retraction tube upon retraction of the handle.

20. The self-expanding stent delivery system according to claim 14, wherein the inner tube surrounds the stent along about 40% to 60% of the entire length of the stent.

21. A self-expanding stent delivery system for delivering a self-expanding stent to a predetermined location in a body lumen, the self-expanding stent delivery system comprising:
a catheter body having a proximal end and a distal end, the catheter body being configured and arranged to carry the stent near the distal end of the catheter body for transporting the stent to the predetermined location in the body lumen for deployment;
a retractable outer sheath configured and arranged to surround the stent and contain the stent in a delivery configuration such that the stent has a reduced radius along its entire axial length; and
a proximal retraction handle connected to the proximal end of the catheter body,
the retractable outer sheath comprising
an outer tube having a distal end portion configured and arranged to surround the stent along the entire length of the stent and having a proximal end portion being connected to the retraction handle, and
a separate inner tube being disposed concentrically within the outer tube and having an end portion configured and arranged to surround the stent only along a part of the entire length of the stent;
the handle comprises a retraction tube being connected at its distal end to the proximal end portion of the outer tube, the refraction tube concentrically surrounding the proximal end of the catheter body and a proximal end portion of the inner tube, the inner tube comprises a stop member at its proximal end portion that is adapted to be engaged with a stop member of the refraction tube upon retraction of the handle.

22. The self-expanding stent delivery system according to claim 21, wherein the inner tube surrounds the stent along about 40% to 60% of the entire length of the stent.

23. The self-expanding stent delivery system according to claim 22, wherein the separate inner tube is fixed to a shaft of catheter body.

24. The self-expanding stent delivery system according to claim 23, wherein the end portion of the inner tube is a distal end portion of the inner tube.

* * * * *